(12) United States Patent
Keim et al.

(10) Patent No.: US 7,635,665 B2
(45) Date of Patent: Dec. 22, 2009

(54) METHOD AND APPARATUS FOR TREATING STORED CROPS

(76) Inventors: John Raymond Keim, 582 Bell Mawr Pl., Barberton, OH (US) 44203; William Albert Keim, 12234 Driftwood, Ft. Wayne, IN (US) 46845; Michael Joe Keim, 604 Bell Mawr Pl., Barberton, OH (US) 44203

( * ) Notice: Subject to any disclaimer, the term of this patent is extended or adjusted under 35 U.S.C. 154(b) by 145 days.

(21) Appl. No.: 10/878,635

(22) Filed: Jun. 28, 2004

(65) Prior Publication Data

US 2005/0288184 A1    Dec. 29, 2005

(51) Int. Cl.
| | |
|---|---|
| *A01N 47/20* | (2006.01) |
| *A01G 17/02* | (2006.01) |
| *A01G 1/00* | (2006.01) |
| *A23B 7/144* | (2006.01) |
| *A23B 9/18* | (2006.01) |
| *A23L 3/3409* | (2006.01) |
| *B60H 3/00* | (2006.01) |

(52) U.S. Cl. ............... 504/304; 47/58.1 FV; 47/89; 426/318; 426/319; 426/320; 99/474

(58) Field of Classification Search ......... 504/304; 47/58.1 FV, 89; 426/318, 319, 320; 99/474
See application file for complete search history.

(56) References Cited

U.S. PATENT DOCUMENTS

| | | | |
|---|---|---|---|
| 3,128,170 A | 4/1964 | Plant | |
| 4,226,179 A | 10/1980 | Sheldon, III et al. | |
| 4,887,525 A * | 12/1989 | Morgan | ............... 99/476 |
| 5,622,912 A * | 4/1997 | Riggle et al. | ............. 504/143 |
| 5,723,184 A | 3/1998 | Yamamoto | |
| 5,935,660 A | 8/1999 | Forsythe et al. | |
| 6,068,888 A | 5/2000 | Forsythe et al. | |
| 6,432,882 B1 | 8/2002 | Yamamoto | |
| 6,790,469 B2 | 9/2004 | Robbs et al. | |
| 2002/0136839 A1 | 9/2002 | Forsythe et al. | |

OTHER PUBLICATIONS

Lewis, Thornton, Kleinkopf, "Commercial Application of CIPC Sprout Inhibitor to Storage Potatoes", University of Idaho, College of Agriculture, www.info.ag.uidaho.edu/resources/PDFs/CIS1059.pdf, Feb. 1997.

* cited by examiner

*Primary Examiner*—Johann R Richter
*Assistant Examiner*—Alton N. Pryor
(74) *Attorney, Agent, or Firm*—Michael Keim; William Keim; John Keim (57) ABSTRACT

A method and apparatus for applying aerosols of chemical formulations to a stored crop is described. The aerosol may be generated by any suitable means using thermal aerosol generators or "cool" aerosol generators. The improvement is the use of the crop storage facility air in the generation of the aerosol and, or the cooling of the aerosol. An important use of the invention is the application of CIPC to stored potatoes.

8 Claims, 7 Drawing Sheets

Crop Storage Facility — 10

Aerosol Generator — 20

CIPC/air mixture

CIPC solvent mixture inlet

Return air

- Crop Storage Facility — 10
- Aerosol Generator — 20
- Blower — 30
- Mixing Unit — 40
- CIPC/air mixture
- CIPC solvent mixture inlet
- Return air

Figure 6

METHOD AND APPARATUS FOR TREATING STORED CROPS

FIELD OF THE INVENTION

The invention relates to a method and apparatus for applying aerosol chemicals to crops and more specifically, for an apparatus and method for applying an aerosol to root vegetables such as potatoes.

BACKGROUND OF THE INVENTION

The storing of agronomic crops such as potato tubers safely and efficiently has been a longstanding need in the agriculture industry. Many efforts have been made to maximize the time period of storage and to extend the useful life of the stored crop such that it retains its commercial utility and appeal. Generally, this storage involves tightly controlled conditions, such as ventilation, temperature, humidity and light.

Potato tubers, upon harvesting, are in a dormant state and are stored in storage facilities as described for example, in U.S. Pat. No. 4,226,179 to Sheldon III, and U.S. Pat. No. 4,887,525 to Morgan. These storage facilities typically provide controlled ventilation and protection from light to large piles of potatoes, which are typically on the order of 16 feet to 20 feet high, and as large as 130 feet wide by 400 feet in length.

Potatoes are often stored for appreciable periods, resulting in sprouting. The problem of sprouting is extensive, and can result in a diminution in the economic value and edibility of the stored potatoes. In efforts to prevent sprouting, potatoes are frequently stored at cool temperatures, e.g., about 40 degrees F. Although storage at cool temperatures does minimize sprouting, it causes dark color and flavor changes in fried potato products. Higher storage temperatures, as high as 52 degrees F. and above, are used to get good fry color. The higher storage temperatures needed to get good light fry color promote sprouting.

In an effort to control sprouting at the higher storage temperatures needed to get good fry color, chemicals such as isopropyl-N-(3-chlorophenyl) carbamate also known as "CIPC" have also been utilized by the potato industry. CIPC is the most important sprout inhibitor utilized in the commercial storage of potatoes, and is especially critical for potatoes used in the manufacture of French fries and potato chips, as consumers desire these products to have a light fry color and good flavor.

CIPC inhibits sprouting by inhibiting cell division. In order for CIPC to be beneficial, every potato eye must be treated. Thus in order to successfully apply CIPC in the large potato piles of the storage facility, CIPC is typically in the form of an aerosol of fine particles that scatter visible light and are therefore visible to the eye as a smoke or fog and which allow the aerosol to be evenly distributed to the potatoes utilizing diffusion.

Figure 1A:
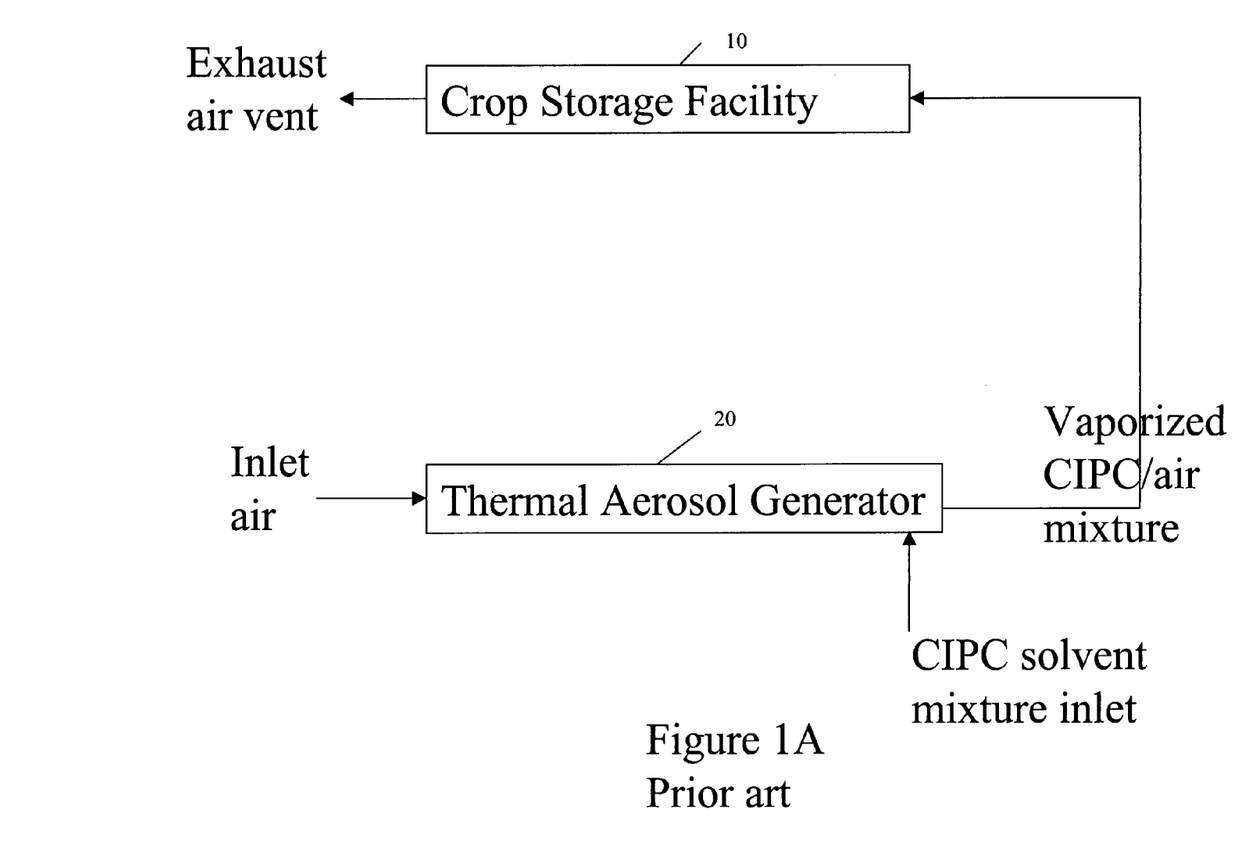
FIG. 1A is a schematic view of a prior art thermal aerosol generator system for a crop storage facility.

In order to generate an aerosol or fog of CIPC, thermal aerosol generators are typically used as shown in FIG. 1A. These thermal generators utilize air taken from outside the storage facility, which is then heated to a high enough temperature to vaporize a suitable CIPC formulation, for example melted solid CIPC or a CIPC solvent solution. Typically, the CIPC vapor/air mixture has an exhaust temperature anywhere from about 700 degrees F. to about 850 degrees F. When the hot CIPC vapor/air mixture is introduced into the much cooler storage facility, a fog or aerosol of CIPC is formed.

A major disadvantage to the use of these thermal foggers is that they heat the CIPC formulation to very high temperatures, which can be a fire hazard. The autoignition temperature of CIPC and its typical formulations is about 734 degrees F. Thus, under the normal operating conditions of a thermal fogger machine, the CIPC vapor air mixture exiting the machine is typically about 800 degrees F., well above the autoignition temperature of CIPC. If the concentration of the CIPC or mixture with other combustibles exceeds its lower flammable limit, the CIPC or its mixture can ignite and burn. Another disadvantage is that the temperature of the CIPC vapor mixture greatly exceeds the autoignition temperature of ordinary combustibles such as for example, paper and wood. Possibly the single greatest threat of fire to a potato storage facility is caused by the autoignition of ordinary combustibles.

Another disadvantage to prior art systems such as shown in FIG. 1A is that outside air is used by the thermal aerosol generator and introduced with the CIPC into the storage system. Thus, in order to maintain a mass balance within the storage system, air and consequently CIPC must be vented from the storage system. As a result, CIPC is exhausted into the environment and thus contributes to pollution, as well as reducing the overall system efficiency. The system inefficiency is also referred to as a displacement loss.

Thus, an improved method and apparatus is desired for generating an aerosol of sprout inhibitors which has a reduced incidence of fire and the improved system efficiency.

SUMMARY OF THE INVENTION

The invention provides in one aspect an improved method for treating crops contained within a storage facility, and treating the crops with an aerosol of a chemical formulation, the method comprising the steps of: generating an aerosol of said chemical formulation from an aerosol generator, mixing the output of said aerosol generator with a source of cooling air where possible to reduce the mixture's temperature to a safe level, and providing said storage facility with the mixture of said cooling air and said aerosol. The source of aerosol generation air and, or cooling air may comprise ambient air, air from the potato storage facility or mixtures thereof. The use of crop storage facility air is beneficial to the aerosol application and is the focus of the invention.

The invention provides in a second aspect a method for treating potatoes contained within a storage facility and treating the potatoes with an aerosol of a chemical formulation, the method comprising the steps of: providing a portion of storage facility air to an aerosol generator, generating an aerosol of said chemical formulation from an aerosol generator, and providing said storage facility with said aerosol.

The invention provides in a third aspect an apparatus for providing an aerosol of a chemical formulation to a potato storage facility, the apparatus comprising: an aerosol generator having an inlet for receiving air that may be sourced from the crop storage facility and a mixing unit having a first inlet end connected to an exhaust end of said aerosol generator, and a second inlet end for receiving air that may be sourced from the crop storage facility, and an exhaust end in fluid communication with said potato storage facility. Some portion or all of the air sourced for the aerosol apparatus is crop storage facility air.

BRIEF DESCRIPTION OF THE DRAWINGS

The invention will be described by way of example and with reference to the accompanying drawings in which.

DETAILED DESCRIPTION OF THE INVENTION

Figure 1B:
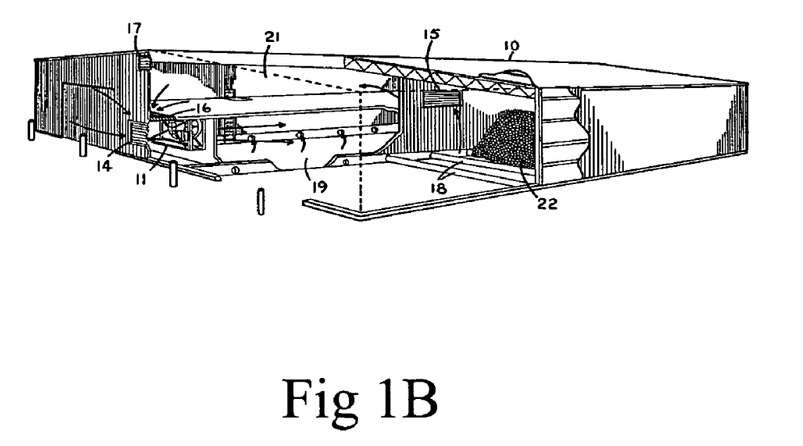
FIG. 1B is a schematic view of a typical crop storage facility.

FIGS. 2-6 illustrates systems and methods of the present invention. As shown in the figures, a crop storage facility 10 like the crop storage facility in FIG. 1B is provided. The crop storage facility comprises a building 10, a central air supply plenum 19, and ventilation pipes 18 connected to the air supply plenum for distributing air across the bottom of the potato pile. Air passes through ventilation holes (not shown) in the ventilation pipes and then filters up through the entire pile of potatoes. Air exiting through the tops of the potato piles passes through plenum return louver 15 into return air plenum 21. The air may then be exhausted outside the building through exhaust line 17, or returned back to the air plenum via fan 11. One skilled in the art may appreciate that there are many variations of crop storage facilities, but they typically maintain the crops at storage temperatures in the range of about 40 to about 52 degrees F. The crop storage facility 10 may further provide controlled relative humidity of the circulating air flow.

An aerosol generator 20, as shown in FIG. 1A, is also provided for vaporizing a chemical formulation, preferably a pesticide. One type of chemical pesticide which may be used with the invention is CIPC. CIPC is also known as chlorpropham or isopropyl-N-3-chlorophenylcarbamate. Chemical formulations include CIPC in both the solid or liquid state which may be in a technically pure form (solid) or mixed with a solvent (liquid), typically a polar organic solvent such as methanol. One formulation which would work with the invention is known by those skilled in the art as 7A, which is a 78.5% CIPC, 21.5% methanol mixture by weight, sold under the trade name Clean CROP Sprout NIP 7 Aerosol, Platte Chemical Co., Greeley, Colo.

Any conventional thermal aerosol generator or cool aerosol generator may also be utilized by the invention. For example, one type of thermal aerosol generator which may be used is the LECO machine, manufactured by Lowndes Engineering Co., of Valdosta Ga. The LECO machine intakes ambient air which is then heated to a high temperature in order to vaporize the CIPC. After vaporization the temperature of the gas stream is on the order of 800 degree F. When the vaporized CIPC is introduced into the much cooler storage facility 10, the CIPC aerosol is formed. Another commercial thermal aerosol generator which would work with the invention is the TIFA machine, manufactured by Todd Shipyard Corp. of Houston Tex. The TIFA machine is also similar in design to the LECO machine, in that it heats ambient air to vaporize CIPC. However, the TIFA machine dilutes the hot CIPC mixture with ambient air at the machine. This ambient air would be replaced with storage air, in one embodiment of the invention as described in more detail, below. A type of cool aerosol generator which would work for the invention is described in U.S. Pat. No. 4,226,179 to Sheldon, III. The Sheldon patent teaches an ultrasonic nozzle. Again, ambient air would be replaced by storage air in a preferred embodiment of the invention.

Figure 2:
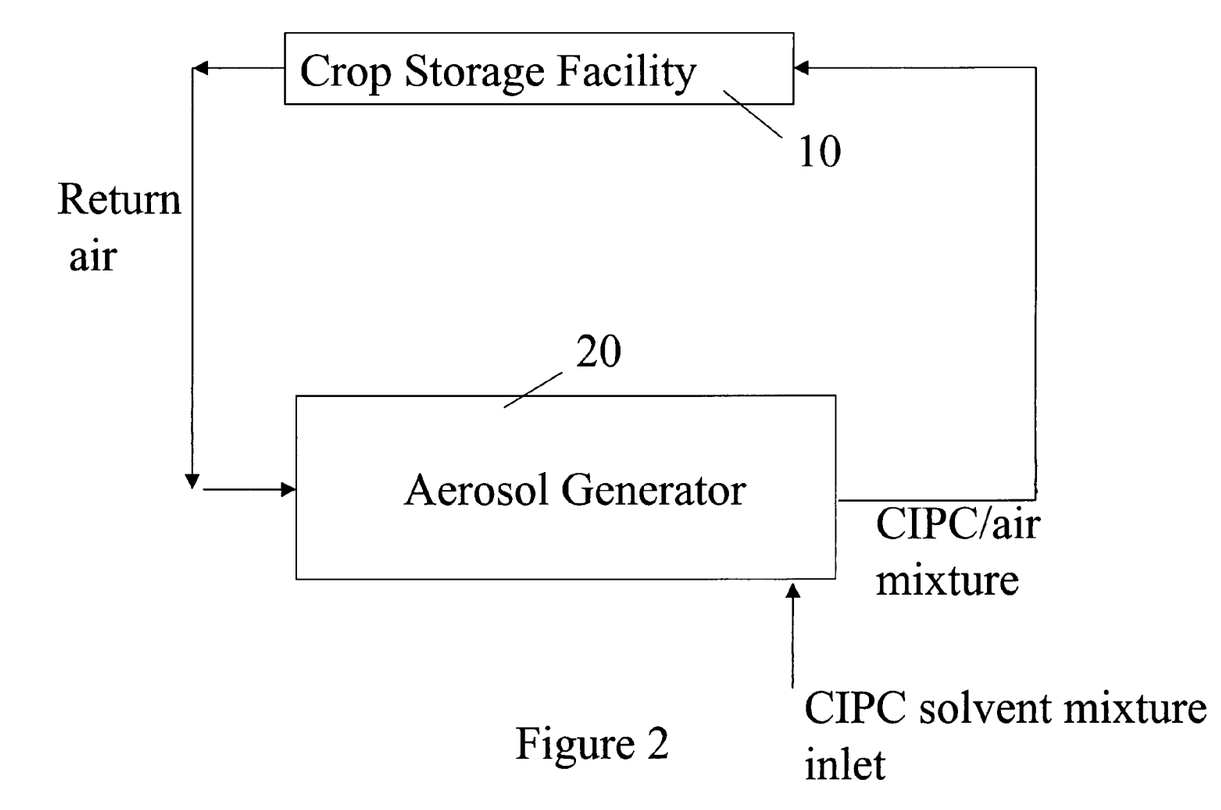
FIG. 2 is a schematic view of an improved system of the present invention utilizing an aerosol apparatus for a crop storage system.

FIG. 2 illustrates a first embodiment of the overall system of the invention comprising the crop storage facility 10 and an aerosol generator 20, preferably a thermal aerosol generator. The air intake to the thermal aerosol generator preferably uses storage facility air to generate a vapor stream that is introduced into the storage facility in the normal manner. If storage facility air is utilized, no air needs to be vented from the system as a result of aerosol generation and introduction. The air intake mixture may also comprise a mixture of air from the crop storage facility and ambient air. The air intake mixture may comprise storage facility air in the range of about 10% to about 100% by volume of the mixture, and ambient air from outside the facility in the range of about 90% to about 0% of the volume of the mixture. Whereas mixtures with outside air may be used as an embodiment of the invention, it is less preferred because the introduction of outside air increases the displacement losses.

Figure 3:
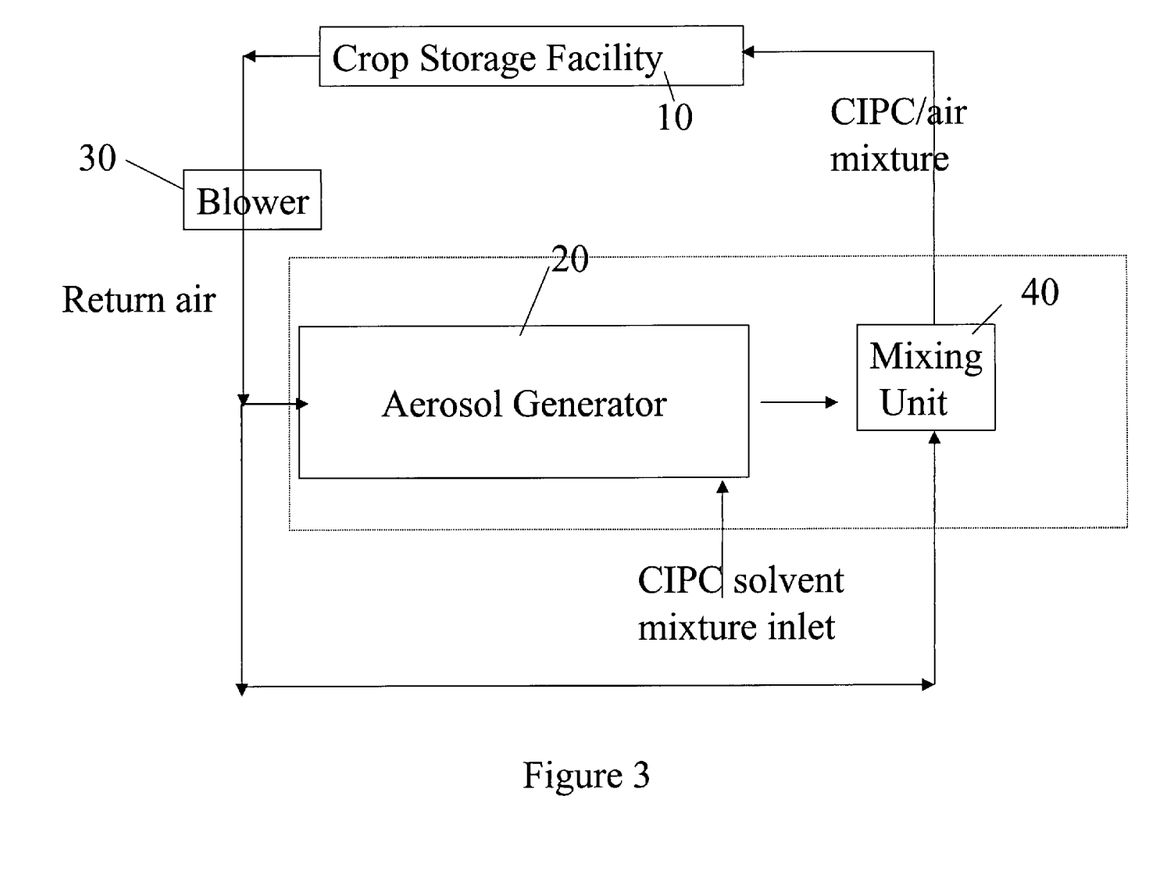
FIGS. 3-6 are schematic views of alternate embodiments of the present invention utilizing an aerosol generator and mixing unit for a crop storage system.

FIG. 3 illustrates a second embodiment of the invention. Like the system shown in FIG. 2, the intake air to the aerosol generator 20 is storage facility air and additionally storage facility air is mixed with the discharge of the aerosol generator to cool the mixture to a safe temperature. The aerosol generator is preferably a thermal aerosol generator. A blower or fan 30 is utilized to facilitate air flow from the crop storage facility 10 to the aerosol generator 20 and to a mixing unit 40.

The mixing unit 40 may be comprised of a pipe, preferably having a length and diameter sized for laminar flow, and having a first inlet for receiving exhaust from the aerosol generator, and a second inlet end for receiving cooling air, preferably from the potato storage facility. Alternatively, ambient air, or a mixture of ambient air and air from the potato storage facility may be the source of cooling air provided to the second inlet end. The hot CIPC air mixture from the thermal generator is mixed with the cooling air by mixing unit 40. The temperature of the hot CIPC mixture may be brought down significantly from 800 degrees F. to about 400 degrees or less, which is well below the autoignition temperature of CIPC and reasonably below the autoignition temperature for ordinary combustibles.

The mixing unit 40 may also comprise readily available industrial mixers such as, for example, the Laminar Blending KM Static Mixer by Chemineer, Inc. of Dayton Ohio. One skilled in the art may select other industrial mixers which function to mix two gaseous flow streams and which may preferably be designed for laminar flow of gases.

Figure 4:
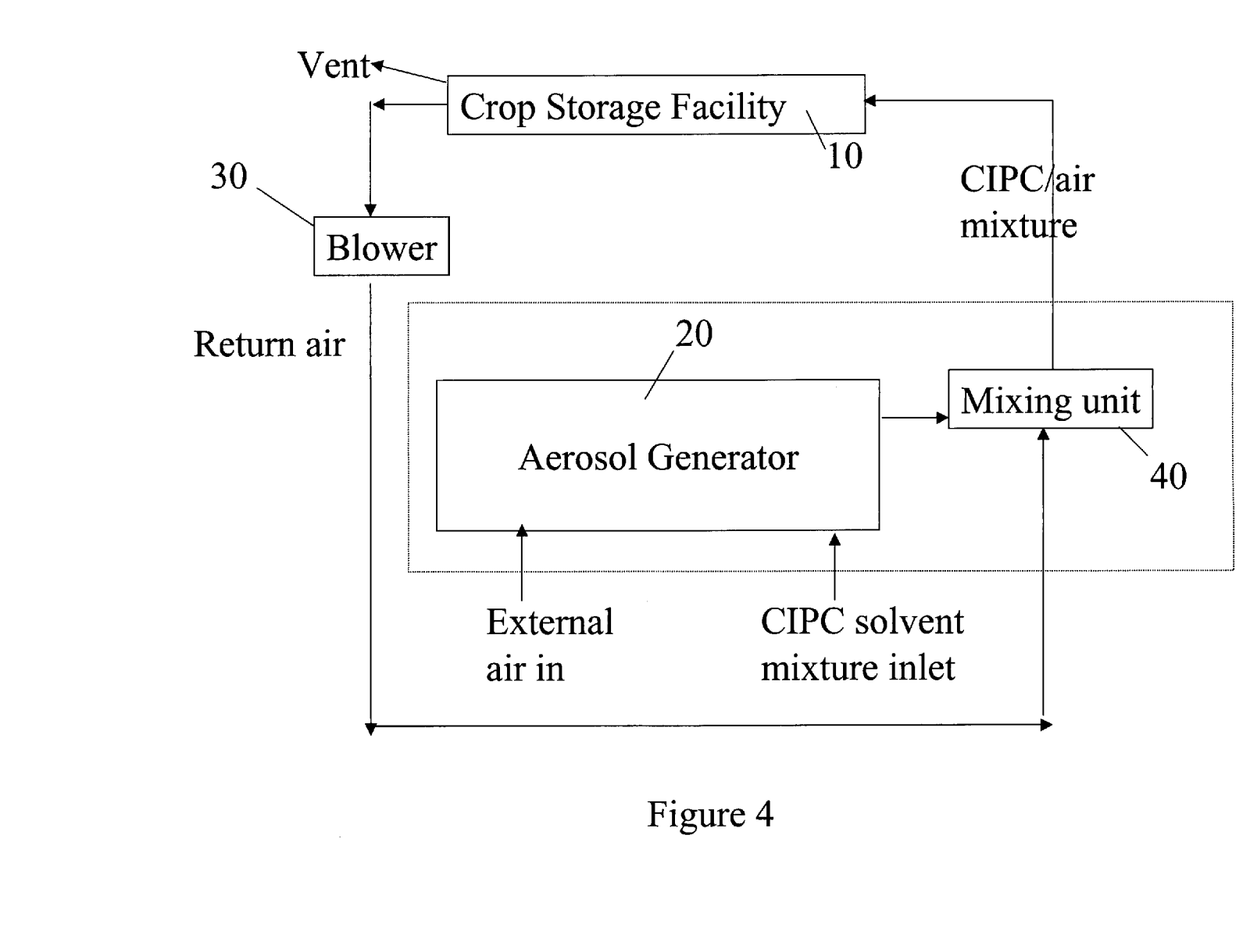

FIG. 4 illustrates yet another embodiment of the present invention. Like the system of FIG. 3, air from the crop storage system is recycled via blower 30 to mixing unit 40. However, ambient air (external to the system) is used to mix with the chemical formulation to form the aerosol. Because ambient air is utilized to generate the aerosol, in order to achieve a mass balance in the system, additional air from the crop storage system is vented. This system has the advantage of being able to cool the hot aerosol below the autoignition temperature of the chemical formulation and to a temperature below the autoignition temperature of ordinary combustibles.

Figure 5:
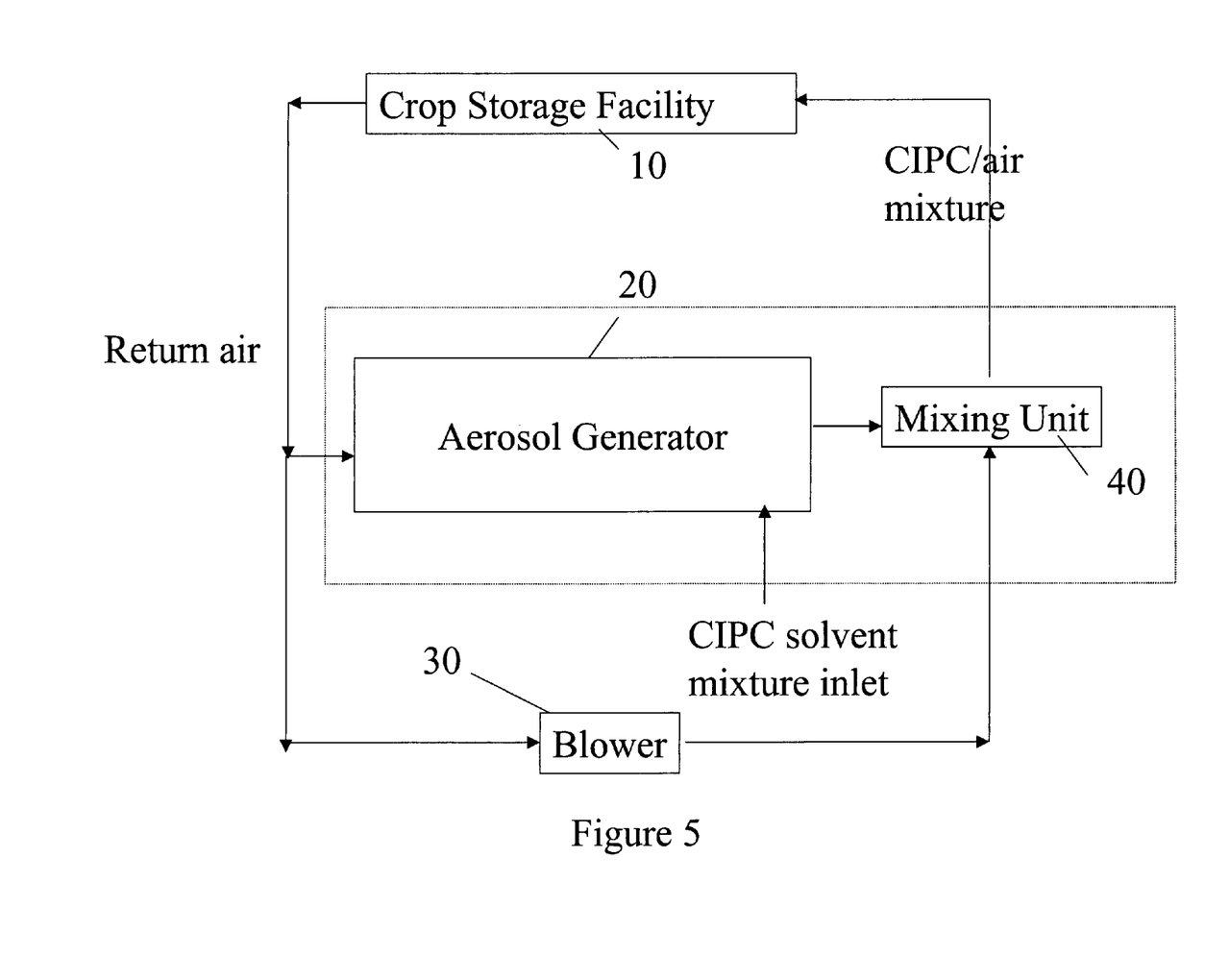

FIG. 5 is yet another embodiment of the present invention. The system in FIG. 5 is very similar to the system shown in FIG. 3, with the exception that the blower unit is moved downstream of the thermal aerosol generator 20.

Figure 6:
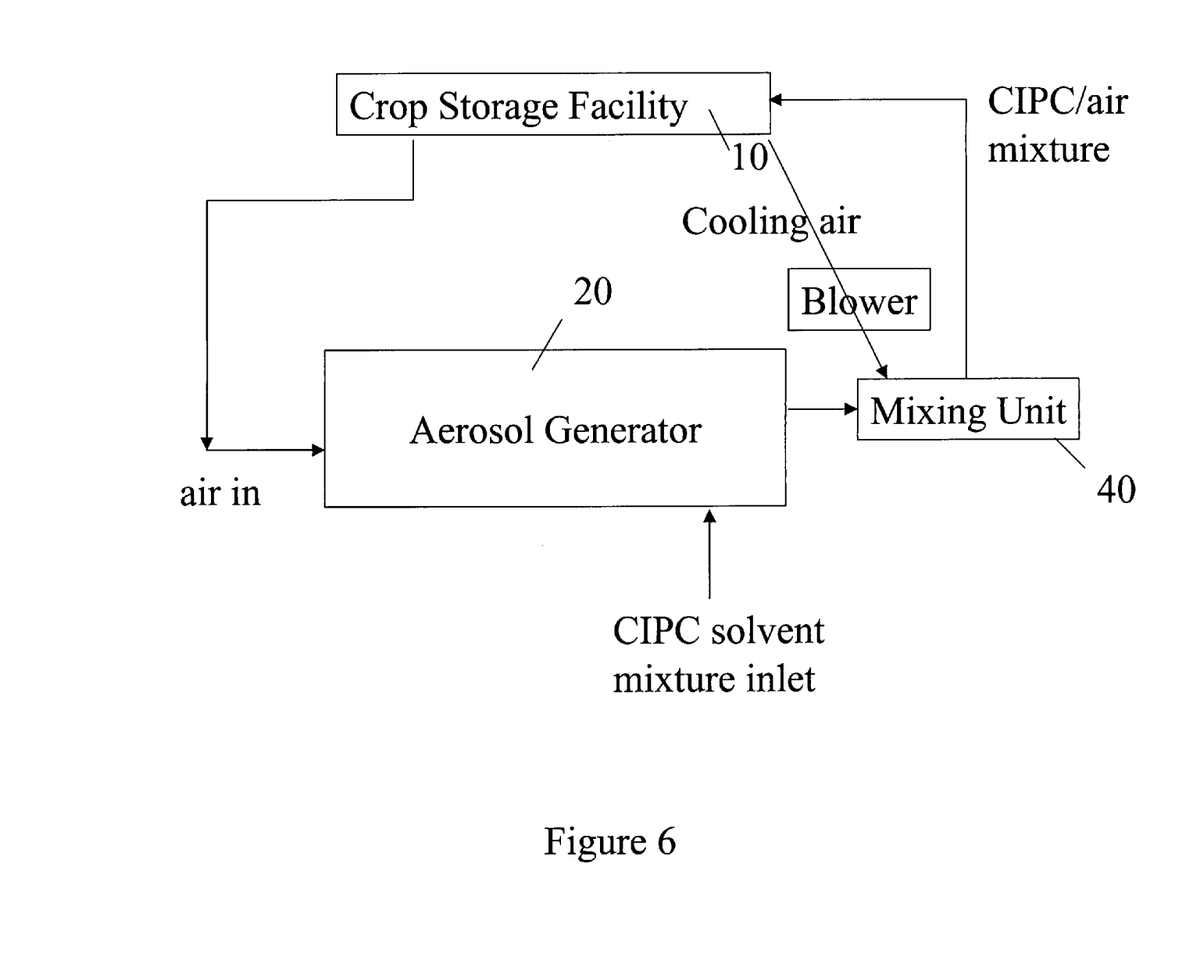

FIG. 6 is yet another embodiment of the present invention. The system in FIG. 6 shows that different storage facility pickup points can be used for the storage facility air that is used by the invention.

The piping connecting the various components described above, particularly between the thermal aerosol generator, the mixing system 40 and the crop storage facility 10, should be of a sufficient size for laminar flow and use large radius bends where needed in order to control particle agglomeration.

While the invention has been described in detail with regards to CIPC, other pesticide chemicals may also be used without departing from the spirit and scope of the invention. For example, the invention may be used with other chemicals such as antimicrobials, fungicides, insecticides, growth regulators, and disease controllers and sub combinations thereof. The different chemicals will have different autoignition temperatures and different flammable limit concentrations that will need to be accommodated.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method for controlling the displacement loss of a chemical formulation when treating crops within a storage facility with an aerosol mixture of a chemical formulation where air intake to an aerosol generator comprises storage facility air in a range of about 10% to about 100% by volume or the mixture and air from outside the storage facility in a range of about 90% to about 0% of the volume of the mixture comprising the steps of:

moving air from a gas re-circulation loop disposed within the storge facility through a first conduit to an inlet of an aerosol generator disposed external to the; storage facility generating with the aerosol generator the aerosol mixture of the chemical formulation using the air from the re-circulation loop;

moving said aerosol from an outlet of the aerosol generator through a second conduit into the building to the re-circulation loop; and moving the aerosol through the re-circulation loop to treat crops stored within the re-circulation loop with the chemical formulation.

2. The method of claim 1 wherein the chemical formulation comprises isopropyl-N-(chlorophenyl) carbamate (CIPC).

3. The method of claim 1 where the stored crops are potatoes.

4. The method of claim 1 further comprising a step of mixing at a location external to the building an exhaust of said aerosol generator with a portion of air from the recirculation loop within the building to form a mixture of the portion of air and the aerosol; and wherein the step of moving the aerosol through the recirculation loop includes moving the mixture through the recirculation loop.

5. The method of claim 4 further including a step of supplying all of the air to be mixed with the exhaust of the aerosol generator from the recirculation loop within the storage facility.

6. The method of claim 4 further including a step of supplying a mixture of ambient air and air from the potato storage facility to be mixed with the exhaust of the aerosol generator.

7. The method of claim 4 wherein the chemical formulation comprises CIPC.

8. The method of claim 4 where the stored crops are potatoes.

* * * * *

(12) INTER PARTES REEXAMINATION CERTIFICATE (0405th)
United States Patent
Keim et al.

(10) Number: US 7,635,665 C1
(45) Certificate Issued: Jul. 3, 2012

(54) METHOD AND APPARATUS FOR TREATING STORED CROPS

(76) Inventors: John Raymond Keim, Barberton, OH (US); William Albert Keim, Wayne, IN (US); Michael Joe Keim, Barberton, OH (US)

Reexamination Request:
No. 95/001,421, Aug. 24, 2010

Reexamination Certificate for:
Patent No.: 7,635,665
Issued: Dec. 22, 2009
Appl. No.: 10/878,635
Filed: Jun. 28, 2004

(51) Int. Cl.
*B60H 3/00* (2006.01)
*A01N 47/20* (2006.01)
*A01N 25/00* (2006.01)
*A01N 25/06* (2006.01)
*A01N 47/10* (2006.01)
*A01G 1/00* (2006.01)
*A01G 17/02* (2006.01)
*A23B 7/144* (2006.01)
*A23B 9/18* (2006.01)
*A23L 3/3409* (2006.01)

(52) U.S. Cl. .......... 504/304; 426/318; 426/319; 426/320; 47/58.1 FV; 47/89; 99/474

(58) Field of Classification Search .......... None
See application file for complete search history.

(56) References Cited

To view the complete listing of prior art documents cited during the proceeding for Reexamination Control Number 95/001,421, please refer to the USPTO's public Patent Application Information Retrieval (PAIR) system under the Display References tab.

*Primary Examiner* — Dwayne Jones (57) ABSTRACT

A method and apparatus for applying aerosols of chemical formulations to a stored crop is described. The aerosol may be generated by any suitable means using thermal aerosol generators or "cool" aerosol generators. The improvement is the use of the crop storage facility air in the generation of the aerosol and, or the cooling of the aerosol. An important use of the invention is the application of CIPC to stored potatoes.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-8 are cancelled.

* * * * *